(12) United States Patent
Hansen

(10) Patent No.: US 12,036,091 B2
(45) Date of Patent: Jul. 16, 2024

(54) 3D SCANNER SYSTEM WITH HANDHELD SCANNER

(71) Applicant: 3SHAPE A/S, Copenhagen K (DK)

(72) Inventor: Kristian Evers Hansen, Birkerød (DK)

(73) Assignee: 3SHAPE A/S, Copenhagen K (DK)

( * ) Notice: Subject to any disclaimer, the term of this patent is extended or adjusted under 35 U.S.C. 154(b) by 881 days.

(21) Appl. No.: 16/495,657

(22) PCT Filed: Mar. 19, 2018

(86) PCT No.: PCT/EP2018/056842
§ 371 (c)(1),
(2) Date: Sep. 19, 2019

(87) PCT Pub. No.: WO2018/172257
PCT Pub. Date: Sep. 27, 2018

(65) Prior Publication Data
US 2020/0022788 A1    Jan. 23, 2020

(30) Foreign Application Priority Data
Mar. 20, 2017    (DK) .......................... PA 2017 70195

(51) Int. Cl.
*G06F 3/0482*    (2013.01)
*A61B 1/24*    (2006.01)
(Continued)

(52) U.S. Cl.
CPC .............. *A61C 9/0053* (2013.01); *A61B 1/24* (2013.01); *A61B 5/0062* (2013.01);
(Continued)

(58) Field of Classification Search
CPC ....... A61C 9/0053; A61B 1/24; A61B 5/0062; A61B 5/0088; G06F 3/0346; G06F 3/0482; G06F 3/04842; G06F 3/04883
See application file for complete search history.

(56) References Cited

U.S. PATENT DOCUMENTS 6,094,197 A * 7/2000 Buxton ................. G06F 3/0482
715/863
7,930,002 B2 * 4/2011 Gong .................... G06F 3/0362
455/574
(Continued)

FOREIGN PATENT DOCUMENTS

CN    103339468 A    10/2013
CN    104837436 A    8/2015
(Continued)

OTHER PUBLICATIONS

Office Action (Notice of Reasons for Rejection) issued on Mar. 22, 2022, by the Japanese Patent Office in corresponding Japanese Patent Application No. 2019-551520, and an English Translation of the Office Action. (4 pages).
(Continued)

*Primary Examiner* — Renee D Chavez
*Assistant Examiner* — Jianmei F Duckworth
(74) *Attorney, Agent, or Firm* — BUCHANAN INGERSOLL & ROONEY PC

(57) ABSTRACT

Disclosed is a 3D scanning system and a method for using such a system, where a handheld scanner of the 3D scanner system is used to control the operation mode of the system such that the user does not need to engage an external unit e.g. during a scanning procedure in which the teeth in a patient's upper and lower jaws are scanned.

14 Claims, 4 Drawing Sheets

(51) Int. Cl.
*A61B 5/00* (2006.01)
*A61C 9/00* (2006.01)
*G06F 3/0346* (2013.01)
*G06F 3/04842* (2022.01)
*G06F 3/04883* (2022.01)

(52) U.S. Cl.
CPC .......... *A61B 5/0088* (2013.01); *G06F 3/0346* (2013.01); *G06F 3/0482* (2013.01); *G06F 3/04842* (2013.01); *G06F 3/04883* (2013.01)

(56) References Cited

U.S. PATENT DOCUMENTS

| | | | | |
|---|---|---|---|---|
| 8,954,887 | B1* | 2/2015 | Tseng | G06F 3/04812 715/823 |
| 11,321,817 | B2 | 5/2022 | Levin | |
| 2006/0062382 | A1* | 3/2006 | Ronkainen | G06F 3/04895 345/184 |
| 2007/0172112 | A1* | 7/2007 | Paley | G06T 1/0007 382/128 |
| 2009/0262074 | A1 | 10/2009 | Nasiri et al. | |
| 2009/0322676 | A1* | 12/2009 | Kerr | G06F 3/0485 345/158 |
| 2010/0037184 | A1* | 2/2010 | Sie | G06F 3/0482 715/863 |
| 2011/0011925 | A1* | 1/2011 | Yoshida | H04N 21/42222 235/375 |
| 2011/0035665 | A1* | 2/2011 | Kim | H04N 1/00411 345/173 |
| 2012/0179035 | A1* | 7/2012 | Boudier | A61B 90/13 378/189 |
| 2013/0257718 | A1 | 10/2013 | Ojelund et al. | |
| 2014/0214430 | A1* | 7/2014 | Wang | H04N 21/42222 704/275 |
| 2015/0138079 | A1* | 5/2015 | Lannsjo | G06F 3/013 345/156 |
| 2015/0320320 | A1* | 11/2015 | Kopelman | A61B 5/0088 433/215 |
| 2016/0259515 | A1 | 9/2016 | Sabina et al. | |
| 2016/0302895 | A1 | 10/2016 | Rohaly et al. | |
| 2017/0038926 | A1 | 2/2017 | Fram | |
| 2017/0083177 | A1* | 3/2017 | Kitada | G06F 3/04845 |
| 2017/0300119 | A1 | 10/2017 | Wu et al. | |

FOREIGN PATENT DOCUMENTS

| | | |
|---|---|---|
| EP | 3098702 A1 | 11/2016 |
| JP | 2017525411 A | 9/2017 |

OTHER PUBLICATIONS

Summons to Attend Oral Proceedings issued in corresponding European Patent Application No. 18 711 941.7-1216, dated Dec. 10, 2021 (10 pages).
International Search Report (PCT/ISA/210) issued on Jul. 4, 2018, by the European Patent Office as the International Searching Authority for International Application No. PCT/EP2018/056842.
Notification of Transmittal of The International Preliminary Report on Patentability (Form PCT/IPEA/416), (Form PCT/IPEA/409) issued on Jun. 19, 2019, in the corresponding International Application No. PCT/EP2018/056842.
Written Opinion (PCT/ISA/237) issued on Jul. 4, 2018, by the European Patent Office as the International Searching Authority for International Application No. PCT/EP2018/056842.
Graetzel et al; "A Non-Contact Mouse for Surgeon-Computer Interaction". Technology and Helth Care, IOS Press, XXX 2003, Switzerland, pp. 1-19.
Vogt et al; "Augmented reality system for MR-guided interventions: phantom studes and first animal test". Proceedings vol. 5367, Medical Imaging 2004 (https://www.spiedigitallibrary.org/conference-proceedings-of-spie/5367/1/Augmented-reality-system-for-MR-guided-interventions--phantom-studies/10.1).
Office Action (Notice to File a Response) issued on Oct. 21, 2022, by the Korean Patent Office in corresponding Korean Patent Application No. 10-2019-7030272, and an English Translation of the Office Action. (14 pages).
First Office Action issued on Jul. 13, 2022, by the Chinese Patent Office in corresponding Chinese Patent Application No. 201880019870.X, and an English Translation of the Office Action. (25 pages).
Search Report issued in European Patent Application No. 23150540.5-1224, dated Apr. 14, 2023 (10 pages).

* cited by examiner

3D SCANNER SYSTEM WITH HANDHELD SCANNER

TECHNICAL FIELD

This invention generally relates to a method and a system comprising a handheld 3D scanner and at least one display where the handheld 3D scanner provides a means for interacting with the control unit of the scanner system.

BACKGROUND

When recording digital 3D representations of a patient's set of teeth by intraoral scanning, the scanning procedure is typically divided into two or more steps. Scanning the teeth in the upper and lower jaws requires two steps and a bite scan providing information about the relative arrangement of the teeth when the teeth are in occlusion forms a third step. The operator needs to enter into the control unit of the scanner system which of the three scans the current scan relates to.

Various user interaction devices are in use for software that controls scan procedures and displays the digital 3D representations recording in the scanning such as: computer mice, space balls, and touch screens. The operation of these interaction devices requires physically touching them. I.e. the dentist needs to remove a hand from the patient and get into contact with the user-interaction device.

Physically touching a user-interaction device can be a disadvantage in medical applications due to risks of cross-contamination between patients or between patient and operator.

Several non-touch user interfaces for 3D data viewing in medical applications have been described in the literature. Vogt et al (2004) describe a touchless interactive system for in-situ visualization of 3D medical imaging data. The user interface is based on tracking of reflective markers, where a camera is mounted on the physician's head. Graetzel et al (2004) describe a touchless system that interprets hand gestures as mouse actions. It is based on stereo vision and intended for use in minimally invasive surgery.

In US 2016/0259515 there is a disclosure of a 3D scanner system having several user-interaction devices.

It remains a problem to improve systems that require user interfaces for interacting with the control unit of the 3D scanner system.

SUMMARY

Disclosed is a 3D scanner system for recording a digital 3D representation of an object by a scanning procedure having at least two steps, wherein the scanner system comprises:
- a handheld scanner capable of recording surface data for the object when operated in a scanning-mode;
- control unit configured for generating a digital 3D representation of the object from the recorded surface data; and
- a display for displaying the digital 3D representation of the object;

where the handheld scanner comprises one or more interaction devices providing for manual interaction with the control unit where:
a first type of activation of the one or more interaction devices provides that the scanner system enters the scanning-mode, and
a second type of activation of the one or more interaction devices provides that the scanner system enters a menu-mode in which a menu comprising one or more menu options is presented on the display and the handheld scanner is configured for selecting among the presented menu options.

The one or more interaction devices provide the advantage that the operator manually can switch between the modes of operation without having to move his hand from the handheld scanner and touching external potential non-sterile equipment.

Entering a menu-mode via the one or more interaction devices provides the advantage that the operator is firstly presented with the menu. The menu thus appears on the display due to the second type of activation of the one or more interaction devices.

Typically, in prior art, a menu is presented to the operator by the touch of a button on a non-integrated device, such as pressing on a mouse, a keyboard, a space ball or the like.

By using the interaction device, integrated in the handheld scanner, the operator is efficiently presented with the menu. Thus, instead of pressing a button on a non-integrated device, the operator may use the hand-held device to enter the menu. At least just this step saves the operator from touching another device. Further, in some embodiments of the scanning system, the user may not be dependent on using other activation devices. In this manner, the operator can enter the menu from the operating location. The operator does not for example need to move to an external computer or touch screen located further away from the operating location to press an activation device connected to the computer or the touch screen.

All in all, this disclosure provides a device to at least efficiently open a menu without contaminating other devices and/or activation devices by touch.

The recorded surface data comprises at least topographical data relating to the topography of the teeth such that the generated digital 3D representation expresses the shape and relative arrangement of the patient's teeth.

In some embodiments, the handheld scanner is capable of recording texture data, fluorescence data and/or IR data.

Other kinds of data can also be recorded from the teeth, such as texture data expressing the shade or color of the teeth or fluorescence data or IR data providing diagnostic information for the teeth. These further kinds of data may be recorded together with the topography data or in a separate step. In the latter situation, the menu provided to the operator in the menu-mode may include the corresponding options.

In some embodiments, the control unit comprises a data processor and a non-transitory computer readable storage medium on which is stored a computer program product with instruction for generating a digital 3D representation from the recorded surface data when the computer program product is executed by the data processor.

Disclosed is a method of scanning the teeth in a patient's upper and lower jaw using a handheld scanner of a 3D scanner system, where the handheld scanner is capable of recording surface data of an object when the system is operated in a scanning-mode, wherein the method comprises:
- entering the scanning-mode of the scanner system by activating a first interaction device of the handheld scanner by a first type of interaction;
- recording surface data for a first one of the jaws while the system is in scanning-mode;
- entering a menu-mode of the scanner system by a second type of interaction with the first interaction device or with a second activation device of the handheld scanner, where the menu comprises one or more menu options displayed on a display of the scanner system;
selecting the desired menu option using the handheld scanner; and
performing the action related to the selected menu option.

As described above the scanning procedure involved in recording digital 3D representations for a patient's teeth often includes a first scanning step in which the teeth in one of the jaws are scanned and a second scanning in which the teeth of the opposing jaw are scanned. Finally, a bite scan is recorded to provide information about how the teeth are arranged in occlusion. In that situation, the scanning sequence may be according to:

Step 1: scan lower jaw to record digital 3D representation of the lower jaw
Step 2: scan upper jaw to record digital 3D representation of the upper jaw
Step 3: record bite scan In some embodiments, the menu options comprise proceeding to the next step in the scanning procedure. In a procedure for recording digital 3D representations of a patient's teeth the next step can e.g. be scanning the jaw opposite to the one that was scanned in the previous step or a bite scan used to detect the relative arrangement of the teeth in occlusion.

In some embodiments, the menu options comprise repeating or continuing the previous step in the scanning procedure. A dentist may choose repeating or continuing the previous step if this was a scanning and inspection of the result of the scanning showing that further data are needed to provide a good coverage of the scanned object.

In some embodiments, the menu options comprise entering an inspection mode in which the view of the displayed digital 3D representation can be adjusted. In the inspection mode, the view of the recorded 3D geometry represented in the display may be determined by the movements of the handheld scanner as determined e.g. by the at least one motion sensor.

If further data are recorded from the teeth, e.g. fluorescence and/or color data these may be viewed together with the digital 3D representation of the teeth in the inspection mode.

In some embodiments, the handheld scanner comprises at least one motion sensor configured for detecting the movement of the handheld scanner at least while operating in the menu-mode and the control unit is configured for translating the detected movement into a selection of a menu option.

The motion sensor may comprise MEMS accelerometers, gyroscope sensors, magnetic sensors, magnetometers, acoustic sensors, optical and infrared sensors, inductive-loop detectors, triboelectric, seismic, inertia-switch sensors, ultrasonic sensors, microwave radar sensors, or sensors based on reflection of transmitted energy such as infrared laser radar, ultrasonic sensors or microwave radar sensors.

The motion sensor is configured for detecting rotation and/or movement of the handheld scanner such that the rotation and/or movement can be translated into a selection of a menu option. This allows the operator to select the desired menu option by turning the handheld scanner in the appropriate direction. E.g. if the desired option is arranged above the center of the displayed menu options, the operator provides a corresponding tilt to the handheld scanner or if the desired option is to the left of the center, the operator turns the distal end of the handheld scanner in that direction.

In some embodiments, the first and second types of activation both are performed with the same interaction device, where the first type of activation comprises a short activation of the interaction device and the second type of activation comprises maintaining the activation of the interaction device until the desired menu option is selected.

In some embodiments, the first and second types of activation are both performed with the same interaction device, and wherein the first type of activation is further configured for changing between a scanning-mode and a non-scanning mode. For example, the same interaction device may be a button, which by a first touch, starts the scanner such that the operator is able to scan a patient. By a second touch, the second touch being similar to the first touch, for example in terms of the time a button being held pressed, the scanner stops scanning.

In some embodiments, when in menu-mode, the scanner system is in a non-scanning mode. Exiting the menu-mode may still leave the scanner system in a non-scanning mode. Upon activation of the first type of activation, the scanning system may be changed from non-scanning mode to scanning mode.

In some embodiments, at least part of the menu options are arranged radially around a center, such as arranged according to a cross or with the options forming at least a partial circle or a partial ring.

In some embodiments, the menu options are arranged concentrically.

In some embodiments, the arrangement of the handheld scanner when entering the menu-mode defines the center. Radially arranged menu options can then be selected simply based on which direction the handheld scanner is turned.

In some embodiments, the selected menu option is to enter scanning-mode and scan the second one of the jaws.

In some embodiments, the interaction devices comprise one or more switches, buttons or contacts.

The interaction devices are preferably arranged on the handheld device such that the operator can engage the interaction devices while holding the handheld device as it is intended to be held during the scanning.

In addition to the scanning-mode the scanner may be capable of entering other recording-modes, such as modes in which it is configured for recording fluorescence or Infra-red light from the teeth, e.g. for diagnostic purposes. The menu may then comprise options relating to these further recording modes.

In some embodiments, the menu options comprise entering a High-Definition mode where the system records a single sub-scan with a higher spatial resolution than used when recording the digital 3D representation.

The present invention relates to different aspects including the system and method described above and in the following, and corresponding systems and methods each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system comprising an intraoral scanner and at least one display, wherein the system can be operated
in a scanning-mode where the intraoral scanner is configured for recording the 3D geometry of a patient's set of teeth; and
in a menu-mode where a menu comprising one or more menu options is presented on the display and the intraoral scanner is configured for selecting among the options provided in the menu;

where the intraoral scanner is adapted for selecting between the modes.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1A:
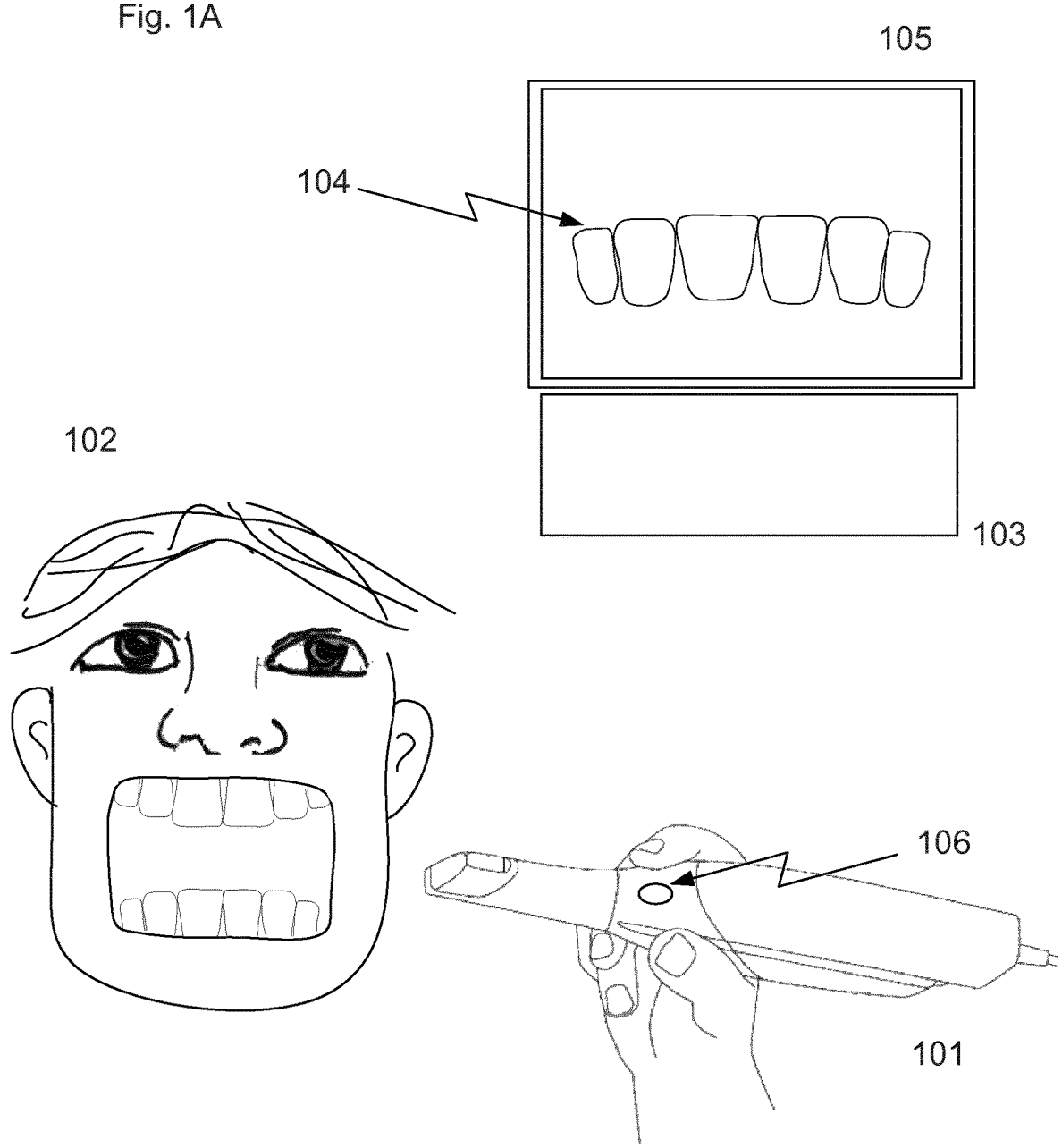
FIGS. 1A and 1B shows a 3D scanner system for intraoral scanning.

FIG. 1A shows a schematic of a 3D scanner system for intraoral scanning.

The system has a handheld scanner 101 and is capable of recording surface data for the patient's 102 teeth when operated in the scanning-mode. The control unit 103 has a data processor and a non-transitory computer readable storage medium on which is stored a computer program product with instruction for generating a digital 3D representation 104 from the surface data recorded by the handheld scanner. The digital 3D representation 104 of the teeth is displayed to on the display 105.

The handheld scanner has an interaction device 106 arranged such that the user easily can reach the interaction device without shifting his grip on the handheld scanner. The interaction device 106 provides for a manual interaction with the control unit such that the user by activating the interaction device can operate the system. The computer program product in the control unit further has instructions for identifying the type of activation provided to the interaction device or the interaction device itself can detect the type and transmitting this information to the control unit.

The scanner system is capable of operating at least in two modes: a scanning-mode and a menu mode. The scanner-mode is entered when the activation of the interaction device is according to a first type of interaction while the menu-mode is entered by a second type of interaction.

In one example of a workflow the system is initially in the scanning-mode and the dentist is ready to start scanning the lower jaw. To start the scanning the operator applies a short press to the contact on the handheld scanner. A first digital 3D representation expressing the shape of the teeth in the lower jaw is then recorded using the handheld scanner. When the dentist believes that he has sufficient data for the lower jaw he activates the menu-mode by pressing and holding down the contact. In the menu-mode he is presented with several options, such as "Inspection mode", "Next" and "Back". The dentist can select the inspection mode by turning the handheld device in the corresponding direction and releasing the contact when the "Inspection mode" option is highlighted.

In the inspection mode, the dentist can inspect the result of the first scanning by viewing the first digital 3D representation from several different views using the handheld scanner to rotate the first digital 3D representation. If satisfied with the result he again presses the contact on the handheld scanner to enter the menu-mode where he points the handheld device towards the "Next" option and releases the contact to proceed to the next step in the scanning sequence. When the dentist and patient are ready the dentist briefly presses the contact and starts scanning the teeth in the upper jaw to record a second digital 3D representation showing the shape of these teeth. When having recorded and inspected the second digital 3D representation the dentist again selects the "next" option in the menu to proceed to recording the bite scan. The bite scan is started when the dentist briefly presses the contact.

Accordingly, the disclosed 3D scanner system provides that the user can record the needed digital 3D representations of the patient's teeth without having to physically engage an external device.

Figure 1B:
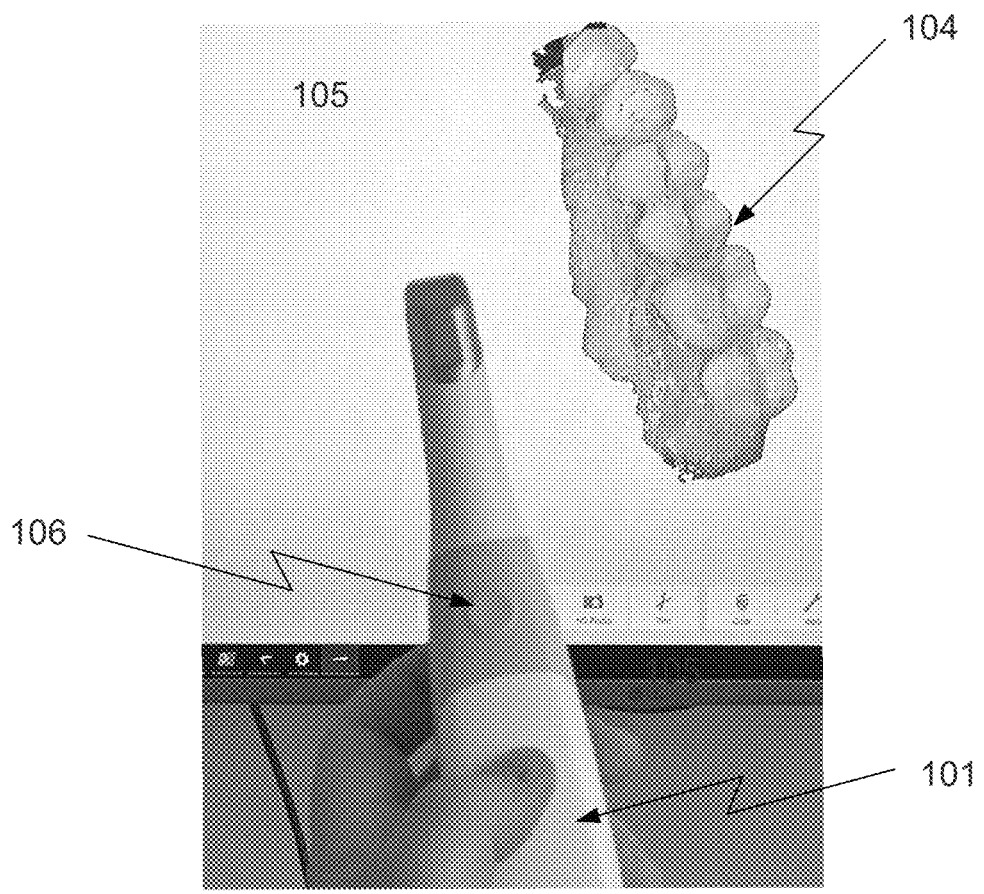

FIG. 1B shows a picture of a handheld intraoral scanner 101 where the contact 106 is arranged such that the user easily can reach it while keeping the scanner in the hand. The user can reach the contact while holding the scanner in the same manner as he will during scanning. In the display 105 is show a digital 3D representation 104 of a some of the teeth in one of the patient's jaws.

Figure 2A:
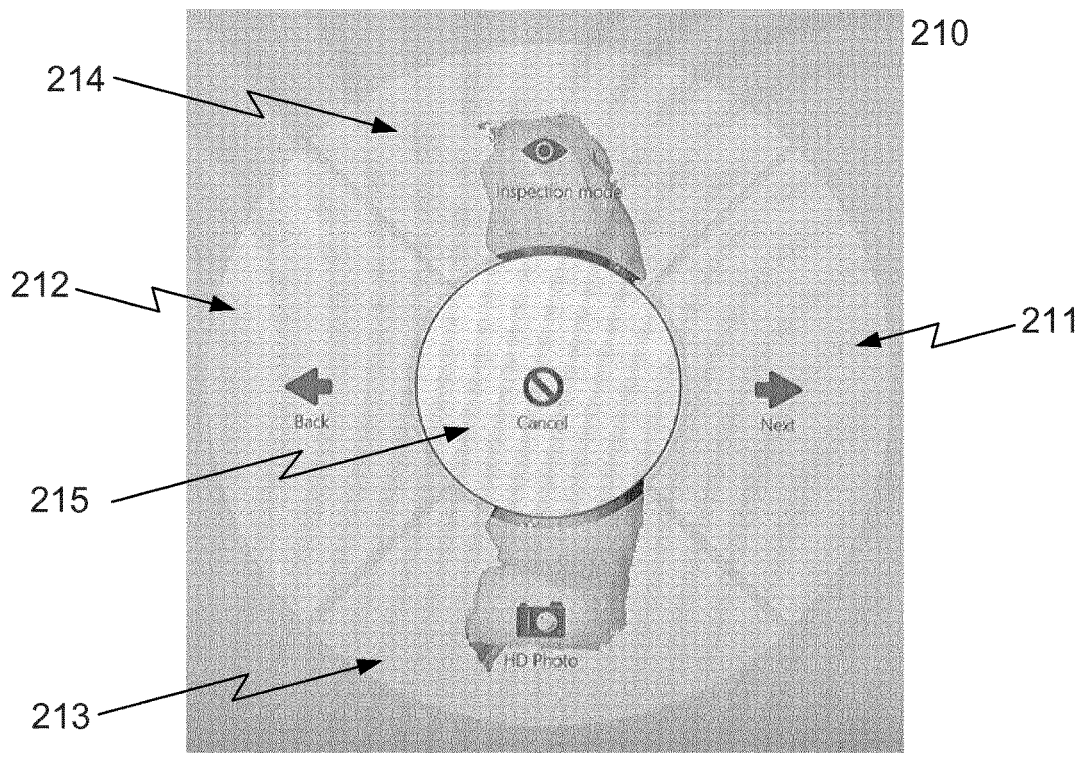
FIGS. 2A and 2B shows an example of a menu.
Figure 2B:
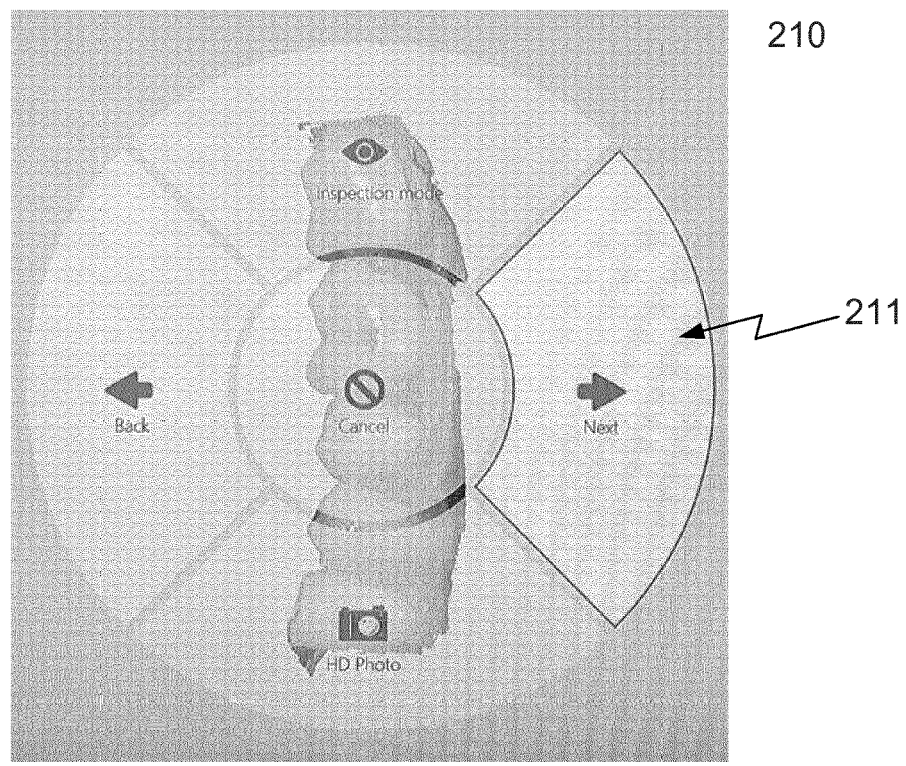

FIGS. 2A and 2B shows screen-shots from a menu presented on the display of the system when the system enters the menu-mode. The menu 210 illustrated in FIGS. 2A and 2B has five options:
1. "Next" 211, i.e. proceed to next step in scanning sequence;
2. "Back" 212, i.e. return to previous step in scanning sequence;
3. "HD photo" 213, i.e. record a single sub-scan of high spatial resolution
4. "Inspection mode" 214, i.e. enter the mode where the previous scan(s) can be viewed
5. "Cancel" 215, i.e. return to previous mode.

The menu is visualized on top of the digital 3D representation recorded in the first step of the scanning procedure. When the system is as described in relation to FIGS. 1A and 1B, the menu-mode is entered when the user keeps the interaction contact pressed. When entering the menu-mode the center part of the menu is highlighted as seen in FIG. 2A indicating the current selection for the next action. Since the center part is the "Cancel" option, releasing the contact with this selection will return the system to its previous mode.

The other four options are arranged radially around the center forming a ring such that the user can select the desired option by turning the handheld device in the corresponding direction. For example, to select to proceed with the next step in the scanning sequence the user turns the handheld scanner towards the right while keeping the contract pressed until the "Next" option is highlighted (as illustrated in FIG. 2B). The user then releases the contact whereby the "next" option is selected, and the scanning system is ready to start the next step in the scan sequence.

Figure 3A:
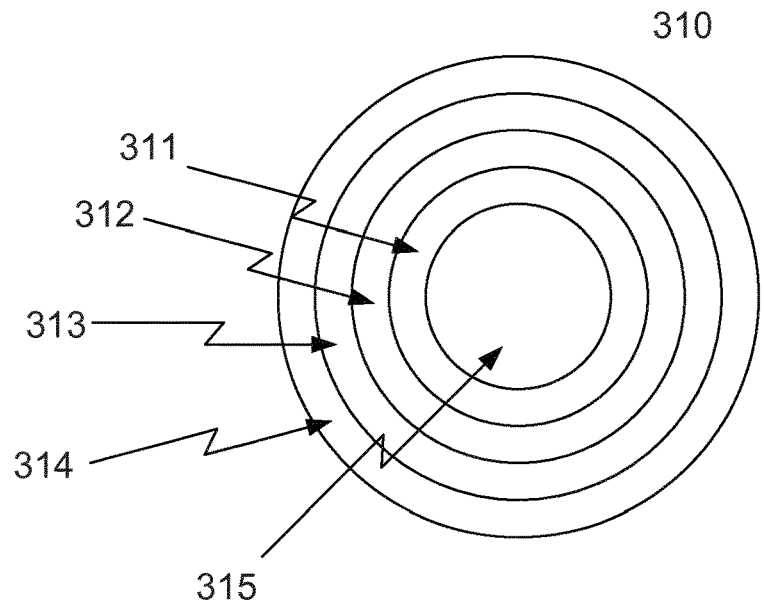
FIGS. 3A and 3B shows more examples of arrangement of menu options on the display
Figure 3B:

FIGS. 3A and 3B shows more examples of arrangement of the options in the menu 310 on the display.

In FIG. 3A the five menu options described in relation to FIG. 2A are arranged concentrically such that the user selects menu option 311, 312, 313, 314, and 315 depending on how much he turns the handheld scanner and not the direction of the turning. Highlighting of the currently selected option can again assist the user in the interaction with the control system.

In FIG. 3B the same five menu options 311, 312, 313, 314, and 315 are arranged in a cross such the selection again is based on the direction of the movement. Further options 317, 318, 319 and 320 may also be added such that the options forms a 3×3 lattice on the display. The further options can e.g. be related to further recording modes such fluorescence or IR scanning/imaging.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A 3D scanner system adapted for intraoral scanning and for recording a digital 3D representation of an object by a scanning procedure of a dental site, the scanning procedure having at least two steps, wherein each of the steps includes forming an image of different sets of a patient's teeth, wherein the 3D scanner system comprises:
    a handheld scanner capable of recording surface data for the object when operated in a scanning-mode;
    control unit configured for generating a digital 3D representation of the object from the recorded surface data;
    a display for displaying the digital 3D representation of the object; and
    at least one motion sensor configured for detecting movement of the handheld scanner;
    where the handheld scanner comprises one interaction device providing for manual interaction with the control unit where:
    a first type of interaction with the one interaction device provides that the 3D scanner system enters the scanning-mode,
    a second type of interaction with the one interaction device provides that the 3D scanner system enters a menu-mode in which a menu comprising a plurality of menu options is presented on the display such that the plurality of menu options are simultaneously displayed, and
    both the first and second types of interaction are performed with the one interaction device, where the first type of interaction comprises a short interaction with the one interaction device and the second type of interaction comprises a press-and-hold long interaction with the one interaction device;
    wherein the presented menu options comprise proceeding to the next step in the scanning procedure, and
    at least part of the presented menu options are arranged radially on the display;
    entering the menu-mode in response to a user performing the second type of interaction;
    while operating in the menu-mode, detecting movement of the handheld scanner by the at least one motion sensor, and selecting a presented menu option from the presented menu options by the control unit of the 3D scanner system when the handheld scanner is moved toward a particular direction and the second type of interaction is released from the one interaction device by the user;
    wherein the second type of interaction is maintained by the user, before the selection of the presented menu option by the control unit where the user handheld scanner movement is translated into a selection gesture.

2. The 3D scanner system according to claim 1, wherein the presented menu options further comprise repeating or continuing the previous step in the scanning procedure.

3. The 3D scanner system according to claim 1, wherein the presented menu options further comprise entering an inspection mode in which the view of the displayed digital 3D representation can be adjusted.

4. The 3D scanner system according to claim 1, wherein the first type of interaction is further configured for changing between a scanning-mode and a non-scanning mode.

5. The 3D scanner system according to claim 1, wherein when in menu-mode, the scanner system is in a non-scanning mode.

6. The 3D scanner system according to claim 1, wherein arrangement of the handheld scanner when entering the menu-mode defines the center.

7. The 3D scanner system according to claim 1, when in menu-mode, returning the 3D scanner system to its previous mode in response to user releasing from the one interaction device.

8. The 3D scanner system according to claim 1, further comprising: while operating in the menu-mode, highlighting one of the presented menu options after another while the second type of interaction is maintained by the user, and selecting a highlighted menu option in response to the user releasing from the one interaction device.

9. The 3D scanner system according to claim 1, wherein at least part of the presented menu options are arranged radially around the center of the display in a form of a circular menu.

10. A method of scanning the teeth in a patient's upper and lower jaw using a handheld scanner of a 3D scanner system, where the handheld scanner is capable of recording surface data of an object when the system is operated to perform a scanning procedure that includes at least two steps and wherein each of the steps includes forming an image of different sets of a patient's teeth in a scanning-mode, wherein the method comprises:
    entering the scanning-mode of the scanner system by interacting with one interaction device of the handheld scanner by a first type of interaction;
    recording surface data for a first one of the jaws while the system is in scanning-mode;
    entering a menu-mode of the scanner system by a second type of interaction with the one interaction device of the handheld scanner, where a menu of the menu-mode comprises a plurality of menu options displayed on a display of the scanner system such that the plurality of menu options are simultaneously presented;

wherein at least part of the presented menu options are arranged radially on the display and the presented menu options comprise proceeding to a next step in the scanning procedure; and both the first and second types of interaction are performed with the one interaction device, where the first type of interaction comprises a short interaction with the one interaction device and the second type of interaction comprises a press-and-hold long interaction with the one interaction device;

while maintaining the second type of interaction, moving the handheld scanner in a particular direction and selecting a desired menu option from the plurality of menu options upon releasing from the one interaction device; and performing an action related to the selected menu option;

wherein the movement of the handheld scanner is detected by the at least one motion sensor and translated by the control unit as a selection gesture.

11. The method according to claim 10, wherein the selected menu option is to enter the scanning-mode and scan the second one of the jaws.

12. The method according to claim 10, further comprising: maintaining the second type of interaction in the menu-mode and highlighting one of the presented menu options after another, and selecting a highlighted menu option upon releasing from the one interaction device.

13. The method according to claim 10, wherein, when in menu-mode, releasing from the one interaction device returns the 3D scanner system to its previous mode.

14. The method according to claim 10, wherein at least part of the presented menu options are arranged radially around the center of the display in a form of a circular menu.

* * * * *